(12) United States Patent
Bar-David et al.

(10) Patent No.: US 11,364,392 B2
(45) Date of Patent: Jun. 21, 2022

(54) METHOD OF EVALUATING A DOSE AS FUNCTION OF DEPTH FOR NONUNIFORM X-RAY BEAMS

(71) Applicant: CONVERGENT R.N.R LTD., Tirat Carmel (IL)

(72) Inventors: Aharon Bar-David, Nesher (IL); Michael Kleckner, Ramat-Ishai (IL); Shirly Borukhin, Atlit (IL); Zeev Burshtein, Nes-Ziona (IL); Avigail Keller, Haifa (IL); Zeev Harel, Kfar-Saba (IL)

(73) Assignee: CONVERGENT R.N.R LTD., Tirat Carmel (IL)

( * ) Notice: Subject to any disclaimer, the term of this patent is extended or adjusted under 35 U.S.C. 154(b) by 0 days.

(21) Appl. No.: 17/071,098

(22) Filed: Oct. 15, 2020

(65) Prior Publication Data
US 2021/0113855 A1    Apr. 22, 2021

Related U.S. Application Data

(63) Continuation-in-part of application No. 16/104,578, filed on Aug. 17, 2018, now abandoned, which is a continuation of application No. PCT/IL2017/050199, filed on Feb. 15, 2017.

(60) Provisional application No. 62/296,610, filed on Feb. 18, 2016.

(51) Int. Cl.
    *A61N 5/10*    (2006.01)
(52) U.S. Cl.
    CPC ......... *A61N 5/1031* (2013.01); *A61N 5/1048* (2013.01); *A61N 5/1077* (2013.01)

(58) Field of Classification Search
    CPC .................................................. A61N 5/1031
    See application file for complete search history.

(56) References Cited

U.S. PATENT DOCUMENTS 6,029,079 A * 2/2000 Cox ..................... A61N 5/1031
                                                          600/407
7,432,510 B2  10/2008 Yeo
            (Continued)

FOREIGN PATENT DOCUMENTS

WO        2016007599 A1    1/2016

OTHER PUBLICATIONS

Standard Imaging. DoseView3D—Better Hardware. Better Software. Better Datahttps://web.archive.org/web/20151223094557/https:/www.standardimaging.com/phantoms/doseview-3d.
(Continued)

*Primary Examiner* — Edwin C Gunberg
(74) *Attorney, Agent, or Firm* — The Roy Gross Law Firm, LLC; Roy Gross

(57) ABSTRACT

A method of evaluating a maximal dose deposited by a non-uniform X-ray beam within a medium comprising the steps of: (a) irradiating said medium by said non-uniform X-ray beam penetrating into a depth of said medium along an axis of said X-ray beam; (b) incrementally measuring a number of transversal dose distributions at successive depths along said axis; (c) determining a maximum dose within each of said number of transversal dose distributions; and (d) calculating a 1-Dimensional depth dependence of said maximal doses obtained from said number of transversal dose distributions.

4 Claims, 7 Drawing Sheets

(56) References Cited

U.S. PATENT DOCUMENTS

| | | | |
|---|---|---|---|
| 7,542,545 B2* | 6/2009 | Nyholm | G01T 1/29 378/65 |
| 8,183,534 B2 | 5/2012 | Lacroix et al. | |
| 2007/0029508 A1 | 2/2007 | Wu | |
| 2007/0153979 A1* | 7/2007 | Baumann | G01N 23/04 378/138 |
| 2010/0034352 A1 | 2/2010 | Aoi et al. | |
| 2011/0282333 A1 | 11/2011 | Herekar et al. | |

OTHER PUBLICATIONS

Sihver, et al. Depth-dose distributions of high-energy carbon, oxygen and neon beams in water. Japanese Journal of Medical Physics, 1998, 18.1: 1-21.

Israeli Office Action for Israeli Patents Application No. 261233, dated Oct. 13, 2021, 3pp.

PCT International Search Report for International Application No. PCT/IL2017/050199, dated May 22, 2017, 3pp.

Written Opinion for International Application No. PCT/IL2017/050199, dated May 22, 2017, 4pp.

Supplementary European Search Report for European Application No. 17752799 completed Jul. 15, 2019, 5pp.

Reza et al. (2005). Development and validation of MCNP4C-based Monte Carlo simulator for fan and cone beam X ray CT, Phys. Med. Biol. 50, pp. 4863-4885. Retrieved Oct. 12, 2021; doi:10.1088/0031-9155/50/20/009.

Britvitch et al. (2013). Real-Time Beam Profile Uniformity Monitoring System, Published in: IEEE Transactions on Nuclear Science, vol. 60, No. 5, pp. 3802-3804; Retrieved Oct. 12, 2021; doi: 10.1109/TNS.2013.2280032.

Sihver et al., Depth-Dose Distributions of High-Energy Carbon, Oxygen and Neon Beams in Water, Jpn. J. Med. Phys. vol. 18, No. 1., Jun. 1, 1998, pp. 1-21. Retrieved Oct. 12, 2021 from: https://doi.org/10.11323/jjmp1992.18.1_1.

* cited by examiner

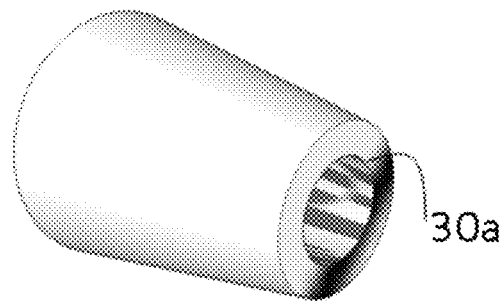
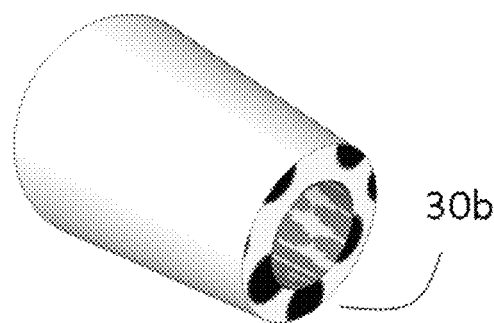
Fig. 3A  Fig. 3B
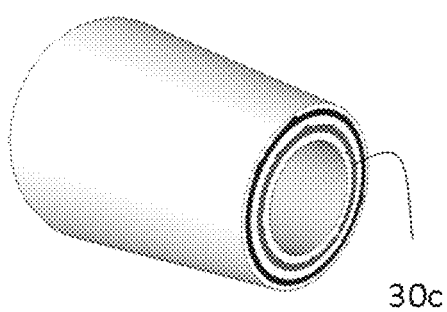
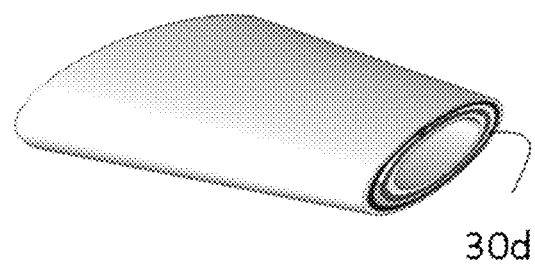
Fig. 3C  Fig. 3D

METHOD OF EVALUATING A DOSE AS FUNCTION OF DEPTH FOR NONUNIFORM X-RAY BEAMS

CROSS REFERENCE TO RELATED APPLICATIONS

This patent application is a continuation-in-part of U.S. Ser. No. 16/104,578 filed Aug. 17, 2018, which is a National Phase of PCT application PCT/IL2017/050199 filed Feb. 15, 2017, which claims the benefit of U.S. Provisional application No. 62/296,544 filed Feb. 18, 2016. The contents of these applications are incorporated by referenced in their entirety.

FIELD OF THE INVENTION

The use of this measure is related to all uses of X-ray producing device. Examples are: Radiotherapy, radiosurgery, imaging device using X-rays etc'. The main fields of use are medical, however one might find the use of the standard also in industrial filed such as Non-Destructive Tests (NDT) as well.

BACKGROUND OF THE INVENTION

Percentage Depth Dose (PDD) curves have been used all over the world for many years in all the fields that use X-Ray radiation. This measure is intended to show the dose distribution as function of depth induced in the bulk of material by the penetration of an X-ray beam without going into the 3D isodose details of a beam penetrating the material in question.

Ordinary PDD curves are shown in a single shot in a single direction where the dose is measured along the center of the beam as function of depth inside the bulk of material, usually water (whose attenuation factor is similar to the one of tissues) or any other tissue equivalent phantom.

The purpose of showing the known PDD curves is usually to evaluate the largest dose absorbed by tissues as function of depth from an instrument having a specific X-ray spectrum when aimed at the material in question.

All today's devices (e.g. LINAC) produce beams whose cross-section has a smooth almost uniform transversal dose distribution with a (usually shallow) maximum at the center of the beam cross-section. The evaluation of largest dose at each depth is why today's PDDs are defined and measured along the center of the beam in a straight line where the maximum dose occurs on a transverse cross-section of the beam at each depth.

A question may arise when the beam irradiated is not uniform and/or not symmetrical, and/or the maximum is not at the center of the cross-section, additionally its points of maximum do not lie in a straight line along the beam propagation axis and may be not continuous.

To illustrate the problem clearly we take the example of a beam whose transversal structure is hollow, i.e. zero radiation along the center and therefore zero dose at the center of its cross-section, the whole shape of the beam may vary, e.g. like cone shape. The internal distributions of dose on cross-sections area at various depths may occur at different points relative to the beams center at each depth. When dealing with radiation producing device on treating and imaging of humans one has to evaluate the maximum dose at each depth for the evaluation of the hazards a human undergoes under imaging and treatments including the efficiency of radio-therapy. In the case of the nonuniform radiation beam that may occur in a complex lens e.g. whose structure is such as generating different interlaced cones shape beams overlapping each other at several different locations along the propagation axis as described in patent U.S. Pat. No. 9,008,271 and/or propagating within a non-uniform medium (e.g. patient's body), radiation pattern in the cross-sectional plane changes with depth of propagation. In terms of radiotherapy, it is important to evaluate the maximal X-ray intensity in each of the transversal cross-sectional planes at each depth along the irradiating X-ray beam and determine the maximum dose relating to the entire transversal plane at each depth. Thus, to determine the maximum dose inflicted by the instrument in a non-uniform beam (e.g. an empty cone) one cannot move in the empty central portion of the beam. Additionally if the internal structure of the beam has a shape where its maximum dose points occur in various different locations relative to the beam axis that might change arbitrarily, or may jump at different places or angles rotationally around the beams axis they may be located not along a straight line and/or not in a continuous line, in simple words, the beam profile shape is constantly changing, then one cannot move always in a straight line.

In the case of non-uniform medium in which the X-ray beam propagates, PDD characterization does not provide adequate information about dose distribution deposed in the medium because different X-ray absorption characteristics tissues of different organs result in different dose absorption in different locations of the patient's body. There is a long-felt and unmet need to provide dose characterization as a function of depth indicating the maximal dose in every depth along the penetration of the non-uniform X-ray beam propagating within the non-uniform medium such as the patient's body.

SUMMARY OF THE INVENTION

It is hence one object of the invention to disclose a method of evaluating a maximal dose deposited by a non-uniform X-ray beam within a medium. The aforesaid method comprises the steps of: (a) irradiating said medium by said non-uniform X-ray beam penetrating into a depth of said medium along an axis of said X-ray beam; (b) incrementally measuring a number of transversal dose distributions at successive depths along said axis; (c) determining a maximum dose within each of said number of transversal dose distributions; (d) calculating a 1-Dimensional depth dependence of said maximal doses obtained from said number of transversal dose distributions.

Another object of the invention is to provide an additional option of the normalized 1-Dimensional depth dependence of said maximal doses obtained from the number of transversal dose distributions.

A further object of the invention is to provide the irradiated medium characterized by non-uniform X-ray absorption.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which:

FIGS. 3A-3D show examples of beam structures inside material depositing non-homogenous dose distribution.

DETAILED DESCRIPTION OF THE INVENTION

Figure 1:
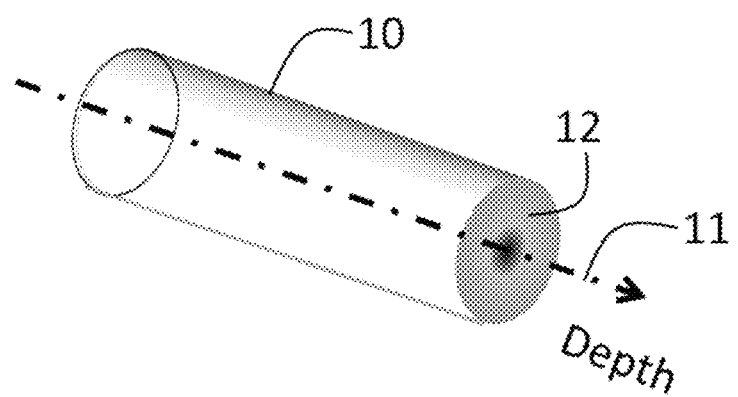
FIG. 1 is a schematic illustration of a common LINAC beam.

The following description is provided, alongside all chapters of the present invention, so as to enable any person skilled in the art to make use of the said invention, and sets forth the best modes contemplated by the inventor of carrying out this invention. Various modifications, however, are adapted to remain apparent to those skilled in the art, since the generic principles of the present invention have been defined specifically to provide a method for the a measure of evaluation of the action of X-ray beams especially in cases where the beam has at least one of the situations where it is not uniform, not symmetrical, not continuous on the transverse direction and or goes through changes along the propagation axis—some or all of them together.

The present invention solves problems regarding the following issues:

Percentage Depth Dose (PDD) refers to the dose which is deposited by todays existing device e.g. LINAC, at the center of the beam at each depth. Such beams have a cross-section where a maximum dose appears at the center of this cross-section. The maximum dose registration is necessary to make sure that no higher dose exists anywhere on the cross-section at each depth. This is done to evaluate the dose a patient receives when a non-uniform x-ray beam is used to image or treat a patient. Thus, for a non-uniform beam, this type of measurements is not adequate in order to achieve the aforesaid purpose, due to the fact that the maximum does not appear generally in the center.

Furthermore, when the function of the maximum dose or maximum dose percentage deposited depending of penetration depth is obtained, it should be taken into account that not all maximum points may lie on the center or the axis of the X-ray beam or any straight line. It is different from the known PDD because it provides the maximal points at each depth regardless their transversal location. It should be emphasized that, in the case of a non-uniform beam, the position of maximal deposited dose can deviate from the beam axis, and might be non-continuous.

The term "Maximal Dose Depth (MDD)" refers to a one-dimensional function of depth that shows the maximum dose at each depth. The units of the function are units of real dose, e.g. Gray. The depth axis is continuous only along the depth direction; thus the location of the points of maxima may lie on a 3 dimensional curve that may be nonlinear and/or not continuous.

The term "Maximal Percentage Dose Depth (MPDD)" is similar to MDD expressed in relative units (per cents). The percentage is relative to the maximum dose of all maxima at all depth, i.e. the maximum of the corresponding MDD function. The difference of the MPDD from the known PDD is that a PDD takes the dose as function of depth along a straight line and is defined at the center of the beam, where as in a non-uniform complex beam, the center may not pass at the maximum of the beam, whereas MPDD is specifically defined to follow the maxima at each depth regardless the shape of its trajectory, thus it may take the highest value of dose at each depth going through a possibly 3 dimensional curve, which might be not along a straight line and might be not continuous, i.e. going through non continuous points on some transversal plane at some depths although covering all points on the propagation axis.

The term "optical axis", is similar to the term "beam axis" and refers to a line connecting an intensity weighted center of gravity of the x-ray source and a center of the target of irradiation in each single directional irradiation shot, which might be as a part of multiple irradiations.

The term "envelope' refers to an overall shape of the beam limited by the criterion of the dose of 1% of its maximum on the local cross-section plane at each depth. The purpose is to relate to beams whose internal structure may differ from its outer structure. For example a beam that has an overall shape of a cone might have internal structure where the points of maximum dose don't lie on a cone shape at all (changing arbitrarily).

The term "TCS" refers to the beam's local 2 dimensional Transversal Cross-Sectional plane (relative to the beam propagation direction) at each depth point.

The term "LCS" refers to Longitudinal Cross-Section cut along the beam propagation direction.

Example of use of the last 2 terms can be: TCS dose distribution—to say transversal dose distribution.

Another example: LCS dose distribution is a longitudinal cut showing dose distribution along the beam propagation.

Figure 2:
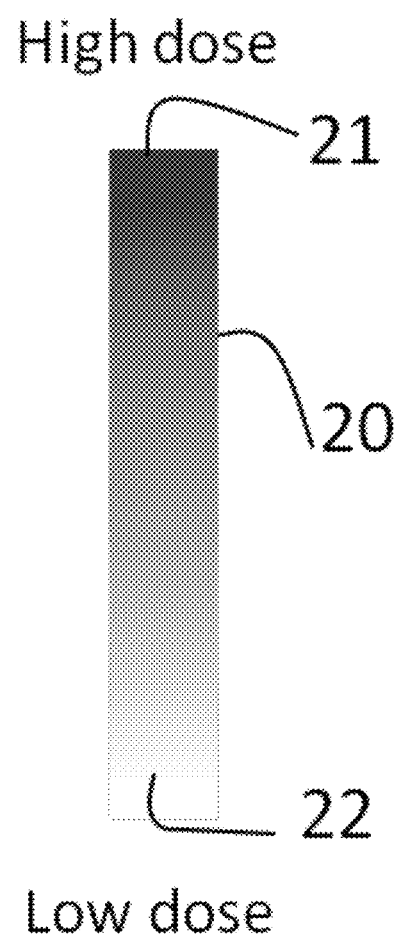
FIG. 2 shows the color description of the dose intensity used in all figures at items showing beam structure where dose intensity is illustrated.

Reference is now made to FIG. 1 illustrating a schematic shape of an exemplary beam provided by a linear particle accelerator (LINAC) having cylindrical envelope 10. Propagation axis 11 is oriented in the direction of depth inward the medium in which the X-ray penetrates. Numeral 12 refers to a cross-sectional dose distribution. The color code corresponding to different doses is shown in FIG. 2. As can be seen the dose is almost uniform and has a maximum in the central portion.

Reference is now made to FIG. 2 illustrating the dose distribution value color code in all relevant parts of all figures by means of a color bar (20). The lower edge (22), white, relates to low dose and the upper end of the bar (21), dark gray color, relates to higher dose.

Reference is now made to FIG. 3 showing exemplary X-ray beams having a cone shaped envelope with a hollow central part. The TCS dose distributions are shown at the front of each FIG. 30a)-(30d). The color distribution on them should be taken as the color code from FIG. 2. For example (30a) and (30b) show completely non-symmetrical TCS dose distributions. The TCS dose distribution (30b) shows several blobs of high dose not at the center. The TCS dose distribution on (30c) is of several relative thin ring areas of high dose. Since this example has a cone shaped envelope, one can envision that the TCS high dose rings resemble thin cones of high dose in 3 dimensions. FIG. 3d shows a different envelope of an example of elliptical cone.

In general the beam's envelope of any shape and structure is in the scope of the present invention.

Figure 4A:
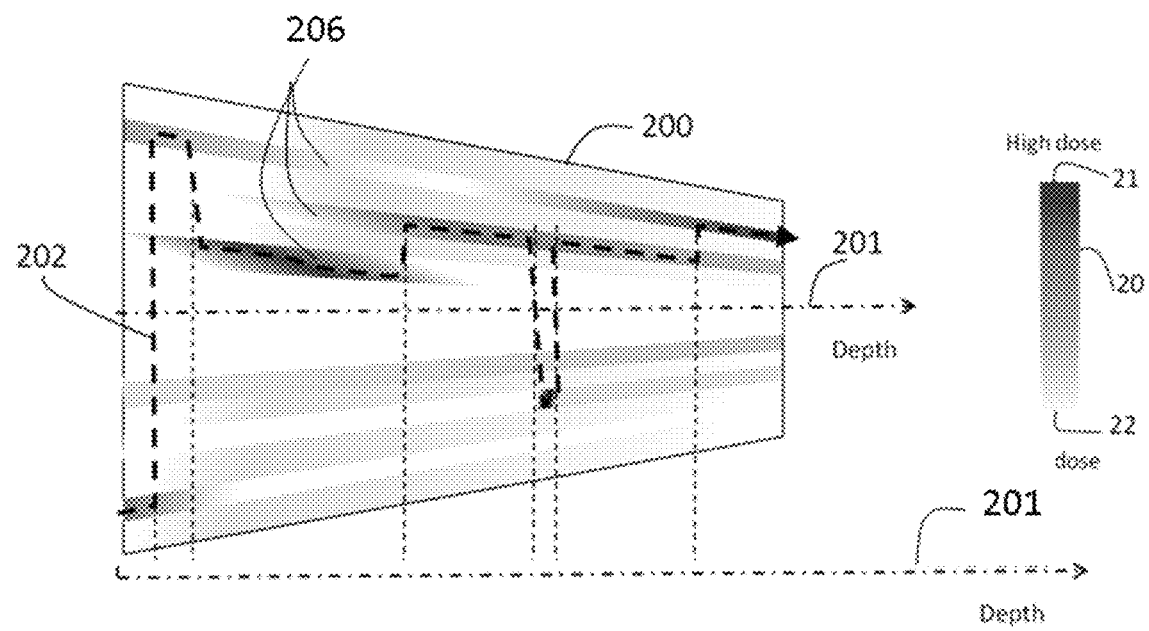
FIG. 4A shows an example of longitudinal cut through material showing a cone shaped beam depositing non-homogenous dose with non-homogenous cone like shaped regions of arbitrary dose distribution with its path through maximum dose points at each depth.

Reference is now made to FIG. 4a Showing an example of an LCS dose distribution of a cone envelope (200) with internal thin cons like dose regions (206) (which would appear as rings on TCS dose distributions). The regions are not uniform and not symmetric. Thus, the track (202) that follows this MPDD (203) along the depth axis (201) is not along a straight line but rather on a line with broken and curved parts that go through the highest dose regions (the darkest areas of each depths in the figure). For simplicity, the maxima dose trajectory is shown on the longitudinal plane of the cut. In general, the trajectory is a 3 dimensional, thus not necessarily lying in a plane. The distribution is shown as an arbitrary dose distribution in order to demonstrate that this method is designed to deal with any distribution.

Figure 4B:
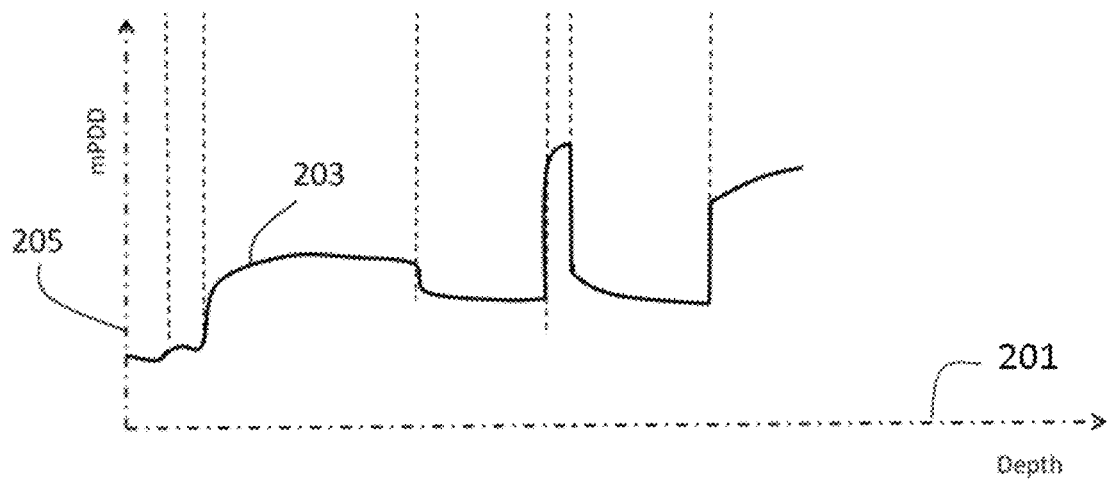
FIG. 4B shows the Maximal Percentage Depth Dose (MPDD) along the same depth axis as FIG. 4A.

Reference is now made to FIG. 4b presenting MPDD curve (203) which shows the dose value at each depth along the depth axis (201). Dose value is on the Y axis (205). FIG. 4b shows the correspondence between dependences of the LCS on the maximum dose obtained on each depth, namely, its MPDD (see dashed lines) on the penetration depth. The value (height) of the curve approximately correlates to the maximum achieved at each depth shown with its color in a schematic manner according to the color code of FIG. 2.

Figure 5A:
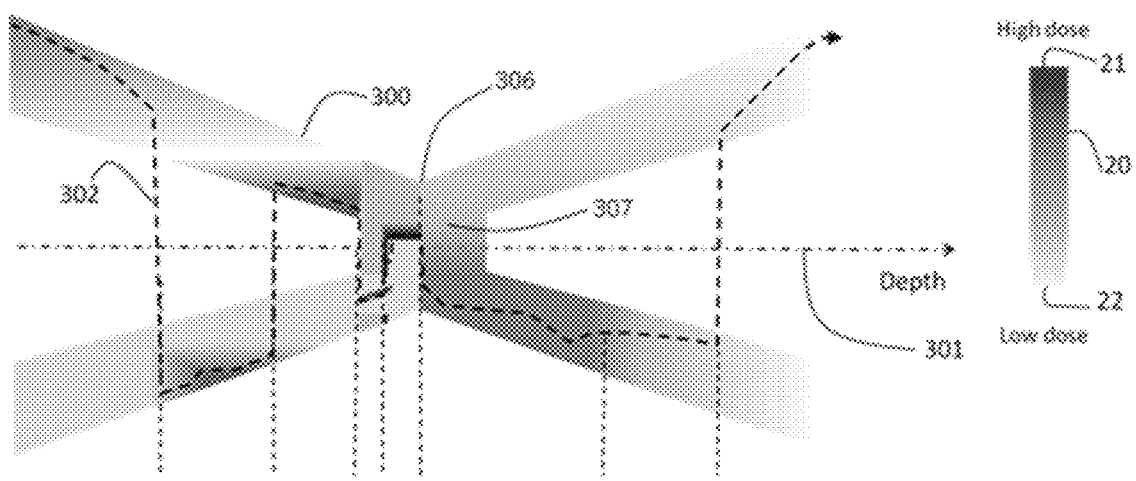
FIG. 5A shows another example of longitudinal cut through material showing a complex shape which converges to a depth and diverges beyond that depth deposing non homogenous arbitrary dose distribution with its path through maximum dose points at each depth on a plane.

Reference is now made to FIG. 5a presenting another example of a more complex beam. Its envelope (300) has a hollow cone structure at shallow depths and converges to a certain depth (306). Beyond this depth it diverges again to a hollow reversed cone. In the middle part (307) it's not hollow and fills the whole bulk. The dose distribution in this example is arbitrary as well. The MPDD track (302) is again a nonlinear broken curved line that goes through the maximum dose at each depth (darkest areas at each depth) with the same rules as before.

Figure 5B:
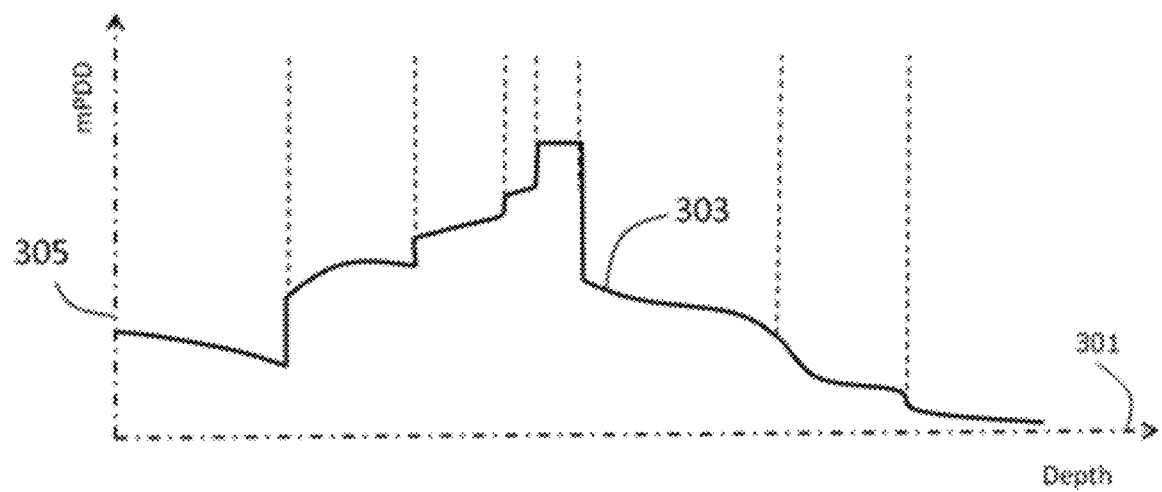
FIG. 5B shows the Maximal Percentage Depth Dose (MPDD) along the same depth axis as FIG. 5A.

Reference is now made to FIG. 5b. The MPDD (303) related to the beam in FIG. 5a is drawn again to match the axis of depth (301) (see dashed lines) with the same rules as before.

The examples of FIGS. 4 and 5 show, for graphical convenience, an LCS dose analysis on a plane longitudinal cut, however, the curve along which the MPDD is taken does not have to lie at all on a plane. The curve may exhibit a 3 dimensional arbitrarily swiveled curved track that may also be not continuous.

Figure 6:
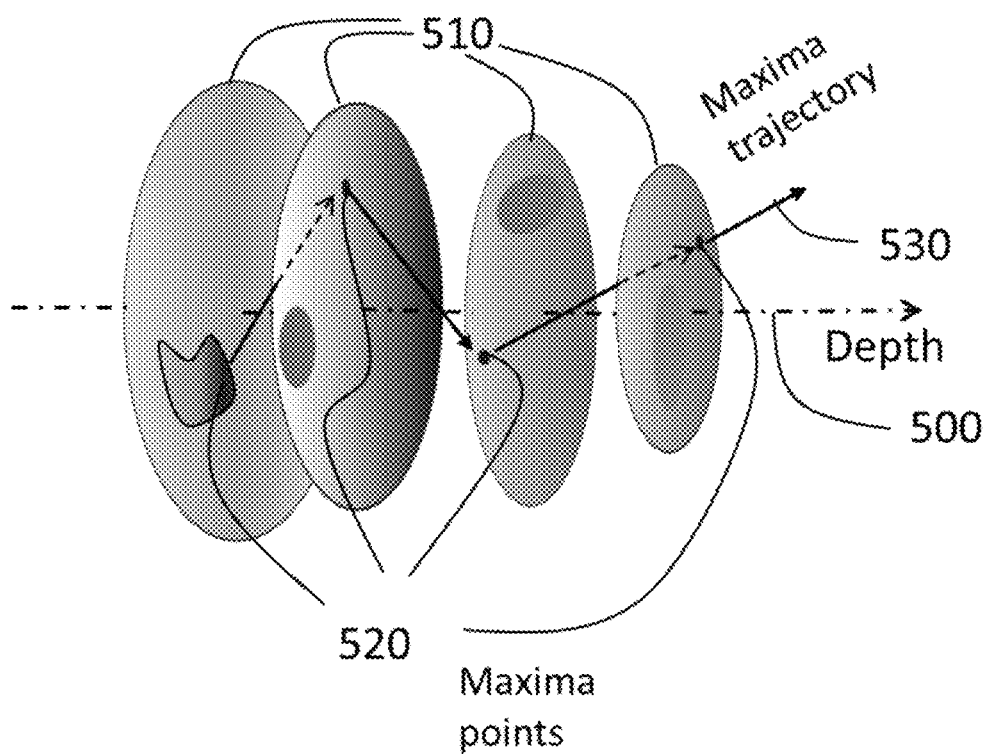
FIG. 6 shows a 3-dimensional drawing of 4 examples of 2 dimensional transversal cuts at 4 locations along the depth.

Reference is now made to FIG. 6. Four examples of transversal cuts (510) located at 4 different depths along the propagation axis (500) are presented. In each plane, one can see arbitrary transversal dose distributions drawn with the same color code as in FIG. 2. In each of those examples, one can see the darkest stains representing the points of highest dose of each separate plane (520). Maxima locations are pointed with arrows (530) and resemble a schematic demonstration of a 3-dimensional trajectory. FIG. 6 is drawn to demonstrate that the trajectory connecting the maxima of the beam along the depths is in general a 3 dimensional entity.

Figure 7A:
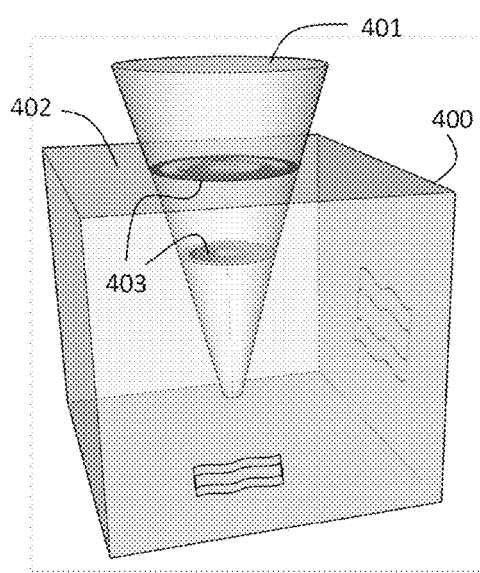
FIG. 7A shows an example of a cone shaped X-ray beam penetrating material with internal intensity structure of rings.
Figure 7B:
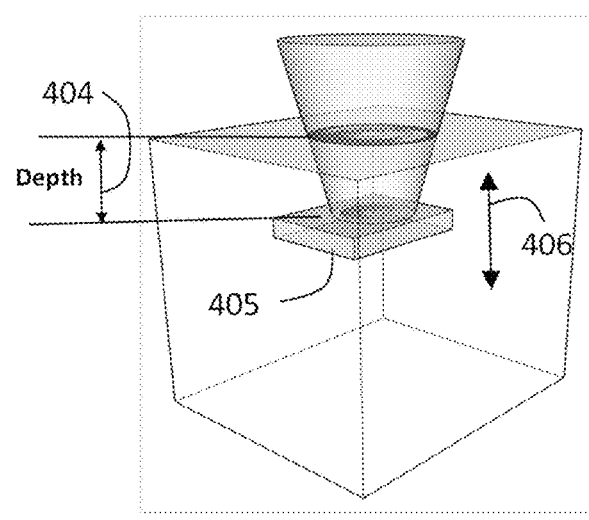
FIG. 7B shows an example of two-dimensional dose distribution measuring device located at specific depth measuring the 2-dimensional distribution on a transversal plane located at a changeable depth.

Reference is now made to FIG. 7a which shows obtaining the non-uniform properties and changing its shape along the propagation axis. FIG. 7a shows an example of a cone shaped X-ray beam (401) penetrating a bulk of material (400) at surface of interface (402) with example of internal intensity distribution of rings (403). A method of measuring MDD or MPDD is illustrated in FIG. 7b. A 2-dimensional array detecting device (405) is placeable at each depth (404) such that a 2-dimensional transversal distribution is taken using a flat panel detector for example. The detecting device is movable along the beam propagation direction with a predetermined increment (406), and maximal dose is obtained at each depth from the 2-dimensional distribution.

The invention claimed is:

1. A method of evaluating a maximal dose deposited by a non-uniform X-ray beam within a medium; said method comprising the steps of:
   irradiating said medium by said non-uniform X-ray beam penetrating into a depth of said medium along an axis of said X-ray beam;
   incrementally measuring a number of transversal dose distributions at successive depths along said axis;
   determining a maximum dose within each of said number of transversal dose distributions;
   calculating a 1-Dimensional depth dependence of said maximal doses obtained from said number of transversal dose distributions.

2. The method of claim 1, comprising a step of normalizing said 1-Dimensional depth dependence of said maximal doses obtained from the number of transversal dose distributions.

3. The method of any one of claim 1, wherein the irradiated medium is characterized by non-uniform X-ray absorption.

4. The method of any one of claim 2, wherein the irradiated medium is characterized by non-uniform X-ray absorption.

* * * * *